United States Patent [19]

Weirich et al.

[11] Patent Number: 6,077,665
[45] Date of Patent: *Jun. 20, 2000

[54] RAPID ASSAY FOR INFECTION IN NEONATES

[75] Inventors: Erica E. Weirich, Redwood City, Calif.; Ronald L. Rabin, Rockville, Md.; Yvonne Maldonado, Redwood City, Calif.; William E. Benitz, Palo Alto, Calif.; Leonore A. Herzenberg; Leonard A. Herzenberg, both of Stanford, Calif.

[73] Assignee: The Board of Trustees of the Leland Stanford Junior University, Palo Alto, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/833,677

[22] Filed: Apr. 8, 1997

Related U.S. Application Data

[60] Provisional application No. 60/017,030, May 7, 1996.

[51] Int. Cl.$^7$ .............................. C12Q 1/68; G01N 33/53
[52] U.S. Cl. ............................................. 435/6; 435/7.21
[58] Field of Search ..................................... 435/7.21, 7.2, 435/7.1, 6; 530/387.1

[56] References Cited

PUBLICATIONS

G. Escobar et al., Early discontinuation of antibiotic treatment in newborns admitted to rule out sepsis: a decision rule, Pediatr Infect Dis J. , vol. 13, No. 10, 1994:13:860–6.
W. Lynn et al., lipopolysaccharide–induced stimulation of CD11b/CD18 expression on neutrophils, Journal of Immunology, vol. 147, 3072–3079, No. 9, 1991.
H. Repo et al.,flow cytometric determination of CD11b upregulation in vivo, Journal of Immunological Methods, 164 (1993) 193–202.
H. Fleit, Fc and complement receptor (CR1 and CR3) expression on neonatal human poly–morphonuclear leukocytes, Biol Neonate, 1989; 55:156–163.
R. Lin, Relationships between plasma cytokine concentrations and leukocyte functional antigen expression in patients with sepsis, Critical Care Medicine, vol. 22, No. 10, 1994, 1595–1601.
M. Radetsky, The laboratory evaluation of newborn sepsis, Current Science, 1995, 8:191–199.
D. Anderson, Neonatal neutrophil dysfunction, American Journal of Pediatric Hematology/Oncology, 11(2):224–226, 1989.
N. Abughali, Deficient total cell content of CR3 (CD11b) in neonatal neutrophils, Blood, vol. 83 No. 4, Feb. 15, 1994, pp. 1086–1092.
R. Rivers, The expression of surface tissue factor apoprotein by blood monocytes in the course of infections in early infancy, Pediatric Research, vol. 31, No. 6, 1992, pp. 567–573.

D. Gendrel et al., Procalcitonin as a marker for the early diagnosis of neonatal infection, Journal of Pediatrics, vol. 128, No. 4, Apr. 1996, pp. 570–573.

B. Davis et al., Neutrophil CD64 expression: potential diagnostic indicator of acute inflammationn and therapeutic monitor of interferon–γ therapy, Lab Hematology, 1:3–12.

Spear et al. J. Pediatrics (Jun. 1995) 126: 982–5.

Abughali et al. Blood (Feb. 15, 1994) 83(4): 1086–1092.

Lin et al. Chest (1993) 104(3): 847–53.

ESJM de Bont et al. ACTA Pediactrics (1994) 83: 696–9.

Buck et al. Pediatrics (1994) 93: 54–8.

Gendrel et al. (Apr. 1996) J. Pediatrics 128(4): 570–573.

Weirich et al. J. Pediatrics (Mar. 1998) 132(3): 445–451.

Elbim et al. J. Cardio. Pharmacol. 25(Sup. 2)S66:S70 1995.

Lanza et al. Int.J.Clin Lab Res. 23: 146–150 (1993).

Rebuck et al. Clin Exp. Immunol. (1995) 101: 183–189.

Smith et al. Ped. Res. (1991) 30(4): 355–361.

*Primary Examiner*—Lisa B. Arthur
*Attorney, Agent, or Firm*—Bozicevic, Field & Francis; Pamela Sherwood; Andrei Popovici

[57] ABSTRACT

A rapid assay for infection in immunodeficient patients such as neonates or immunocompromised patients (e.g. HIV or transplant patients) allows diagnosis at initial evaluation, such that antibiotic treatment and confinement to an intensive care unit can be avoided for uninfected patients. The assay can be used for detecting bacterial, viral, or fungal colonization of the blood stream, cerebrospinal fluid (CSF), or urinary tract. The method is particularly useful for sepsis diagnosis. Polymorphonuclear leukocyte (PMN, neutrophil) CD11b (Mac-1, CR3) levels are measured by flow cytometry or laser scanning microscopy in low volume (0.1 ml) whole blood samples. A dual-laser FACS identifies neutrophils by FITC-conjugated anti-CD15 fluorescent antibodies, and identifies surface neutrophil CD11b marked with PE-conjugated anti-CD11b antibodies. Spontaneous upregulation of CD11b is prevented by handling samples at 4° C. or adding a stabilizing compound such as anti-CD14 antibody or adenosine to the samples. A kit comprises calibration markers such as CD11b-coated microspheres for calibrating the device used for analysis according to diagnosis threshold(s).

28 Claims, 6 Drawing Sheets

RAPID ASSAY FOR INFECTION IN NEONATES

RELATED APPLICATION DATA

This application is based on U.S. Provisional Patent Application Ser. No. 60/017,030, filed May 7, 1996, which is herein incorporated by reference.

This invention was made with U.S. Government support under and National Institutes of Health grant No. CA42509. The U.S. Government has certain rights in this invention.

FIELD OF THE INVENTION

This invention relates to the field of diagnosis and treatment of infection, and in particular to a rapid and reliable assay for evaluating neonates and other immunodeficient patients suspected of infection.

BACKGROUND OF THE INVENTION

Every year, 300,000 newborns are treated for infection in the United States, at a cost of over $800 million. While the prevalence of severe bacterial infection in neonates is low (from 1 to 10 per-1000 live births), mortality is high (20–75%) and has not decreased despite the development of potent antibiotics over the last decade. In particular, blood stream infections (sepsis) develop very rapidly, and are often fatal within hours of neonatal exposure to pathogens. Consequently, treatment is often initiated empirically because of nonspecific clinical signs or maternal risk factors, and an average of 17 infants are treated for each one who is truly infected. For general information on neonatal infection including sepsis see for example references [1–6].

Multiple immunologic impairments in neonates, such as low levels of IgA, IgM, and some IgG subclasses, a smaller neutrophil reserve pool than that of adults (10% of adult levels at birth), and functional deficiencies in circulating neutrophils put neonates at risk for serious infection upon exposure to pathogens. Clinical practice thus defines a series of risk factors whose presence dictates clinical decisions aimed at prevention or anticipatory treatment of neonatal infection. See references [7–13] for information on neonatal immune system deficiencies, and references [14–15] for information on neonatal infection risk factors and their relationship to clinical decisions.

Three major preventative and treatment pathways are commonly followed: 1) mothers at risk for vertically transmitting infection (e.g. mothers with known colonization with Group B Streptococcus, premature rupture of membranes, maternal fever, spontaneous onset of labor before term) may be treated perinatally with antibiotics; 2) infants with a single maternal risk factor or who are mildly premature may be monitored for 24 hours in an intermediate or intensive care nursery; and 3) infants with multiple risk factors and/or clinical signs of infection may undergo a complete diagnostic evaluation, including blood and CSF cultures, CBC, and chest X-rays. Treatment with broad spectrum antibiotics is usually initiated, and infants remain in the hospital until infection can be ruled out. For information on neonatal infection treatment using antibiotics see references [4–6, 16].

Currently, some clinicians use serum C-reactive protein (CRP) to exclude the diagnosis of infection in at-risk neonates. CRP is secreted by hepatocytes as a component of the acute-phase response, and increases in serum close to 1,000-fold in response to tissue insult. Serum CRP elevation depends upon the production of IL-6 and TNF-α and their transport to the liver, where CRP is then synthesized. In the absence of clinical signs of infection, three negative CRP measurements on consecutive days provide convincing evidence that an infant is not infected. One positive CRP measurement suggests that infection is a possibility. For information on the use of CRP for diagnosis of neonatal infection see references [17–18].

Serum CRP assays have several disadvantages. The time delay between bacterial exposure and elevated serum CRP may range from hours to days. Consequently, while CRP may help to retrospectively exclude infection and to support discontinuation of antimicrobial therapy, CRP is not commonly used for identifying infants for whom antibiotic treatment may be safely omitted. Moreover, CRP levels in serum may be increased nonspecifically, as is seen in trauma and other forms of physiological stress (see references [19–20]). The use of CRP as an infection indicator may thus lead to unnecessary treatment of uninfected neonates. In addition, serum CRP elevation indicates only bacterial infection, and not viral infection.

Bacterial cultures are also commonly used for diagnosing neonatal infection. Results from bacterial cultures are generally not available for 24–48 hours, after treatment decisionsare commonly made. Thus, bacterial cultures are not used to rule out infection at initial evaluation. Also, bacterial cultures may have high false negative rates at early time points. For information on the use of bacterial cultures for neonatal infection diagnosis see reference [57].

Current well-established diagnostic tests for neonatal infection, including CRP and blood cultures, are confirmatory in nature and are not generally used for making treatment decisions at initial evaluation. Since neonatal sepsis is often fulminant and fatal within hours of exposure to antigen, CRP and bacterial culture tests do not usually eliminate the need to treat and confine at-risk neonates before test results are available.

An article by Davis et al. [69], herein incorporated by reference, describes a quantitative flow cytometric assay for leukocyte high-affinity Fc receptor (CD64) expression, and proposes its use as a diagnostic indicator of systemic acute inflammatory response. The receptor CD64 is not seen to be increased until six hours after exposure to interferon-γ or G-CSF, however. Presumably, the elevation of CD64 is dependent on several levels of protein synthesis, and CD64 levels measured at early time points reflect not only antigen presence but also a particular stage of protein synthesis. In addition, the assay described by Davis et al. requires the use of as much as 100 ml of blood, much more than can be acceptably sampled from a neonate.

Davis et al. also report evaluating a number of potential infection indicators, including leukocyte CD11a, CD11b, CD16, CD18, CD23, CD32, and HLA-DR, and finding no correlation between the expression of the potential indicators and the presence of infection or other laboratory tests.

Gendrel et al. [67] propose a serum pro-calcitonin assay for neonatal infection diagnosis. Pro-calcitonin has not yet proven reliable enough for use as an indicator of neonatal infection, however. While pro-calcitonin is slightly elevated in infants with viral infection, bacterial colonization, or neonatal distress, it is only highly elevated in infants with bacterial sepsis.

Other potential indicators of neonatal infection have been proposed by many investigators, including IL-6, IL-2, hematological scoring systems, gastric aspirate studies, bacterial antigen tests, and more (see references [4, 5, 17, 58–66]).

OBJECTS AND ADVANTAGES OF THE INVENTION

In light of the above, it is a primary object of the present invention to provide a method of rapidly and reliably testing neonates for infection. The testing method is fast and has high positive and negative predictive values. It is another object to provide a testing method that allows excluding infection in neonates at initial evalation for infection. It is another object to provide a testing method that allows excluding infection in neonates before commencement of antibiotic treatment and/or confinement to an intensive care unit. It is another object to provide a method requiring a very small amount of sample blood, in particular an amount small enough to be obtainable as waste from conventional blood draws. It is yet another object to provide a testing method that measures a primary response to antigen, and that does not require antigen-induced protein synthesis. It is still another object to provide a method allowing early identification of viral as well as bacterial infection. It is a further object to provide a test that is relatively simple to perform, and requires little technician time or training. The method allows a reduction in the average length of hospital stay and antibiotic use for neonates suspected of having infection. The reduced use of antibiotics diminishes the selection pressure for antibiotic-resistant organisms, improves neonatal intensive care unit flora, and reduces the incidence of nosocomial infection. The method allows a reduction in the number of hospitalized infants who develop heavy fungal colonization as a result of antibiotic treatment. The method allows a reduction in the time spent by neonates in a neonatal intensive care unit, which in turn increases the time available for bonding between neonates and their parents and reduces delays in the establishment of breastfeeding. It is another object to provide a kit allowing measurement standardization between different devices.

SUMMARY OF THE INVENTION

The present invention provides a reliable neonatal infection assay that is rapid enough for excluding infection in uninfected neonates at initial evaluation, such that antibiotic treatment and confinement to an intensive care unit can be avoided for uninfected neonates. In a preferred embodiment, neutrophil surface CD11b levels are measured by flow cytometry in whole blood samples.

DESCRIPTION OF THE FIGURES

FIG. 3-A shows a FACS scan illustrating neutrophil CD11b expression in an uninfected infant, according to the present invention.

FIG. 3-B shows a FACS scan illustrating neutrophil CD11b expression in an infant infected with Group B Streptococcus, according to the present invention.

FIGS. 4-A through 4-C show distributions of neutrophil CD11b for three clinical outcome groups, according to the present invention.

FIGS. 5-A and 5-B show CRP levels at admission and peak CRP levels for neonates with infection confirmed by cultures, respectively.

DETAILED DESCRIPTION

The term "infection" is understood to refer to a bacterial, viral, or fungal colonization of the patient's blood stream, cerebrospinal fluid, or urinary tract. The term "sepsis" is understood to refer to a blood stream infection. An infection indicator is understood to refer to a molecule whose level indicates whether a patient is infected, and predicts whether the patient will display infection symptoms and/or a positive result on a confirmatory infection test performed after the measurement of the infection indicator level. A rapid infection indicator is understood to refer to an infection indicator whose detection is rapid enough to allow its use in an initial decision to treat and/or confine the patient to an intensive care unit. In practice, the level of a rapid infection indicator can be used to make a treatment decision within less than four hours, preferably within less than two hours, and ideally within minutes or less than half an hour of an initial evaluation of the neonate.

The present invention provides a method of rapidly and reliably testing neonates for infection. The method comprises measuring a level of a rapid infection indicator in a neonate for deciding whether to treat the neonate for infection. For a population of neonates, measuring the levels of the rapid infection indicator in the population allows identifying a treatment group and a treatment exclusion group from the population, according to the measured levels. The treatment group is treated for infection, while the treatment exclusion group is excluded from infection treatment. The evaluated population preferably consists of neonates considered to be at risk for infection due to maternal risk factors and/or neonate symptoms.

Preferably, infected neonates are neonates who are later confirmed to be infected by bacterial, viral or fungal cultures, or neonates later suspected to be infected due to persistence of infection symptoms or a positive result on a reliable confirmatory test such as a CRP test. Similarly, uninfected neonates are neonates who are later determined to be uninfected by lack of persistent infection symptoms, and/or negative cultures and negative results on reliable confirmatory tests.

Because of the severe consequences of misdiagnosing infected neonates, it is particularly desirable that the treatment group comprise substantially all infected (including septic) neonates in the population. Equivalently, the treatment exclusion group consists substantially of uninfected neonates. It is important that a neonatal infection test of the present invention have a very low false negative rate. It is thus important that the test have a high negative predictive value (probability that a negative result is correct) and sensitivity (number of infected patients detected by the test as a fraction of actual number of infected patients). The negative predictive value and sensitivity of the test are higher than 90%, preferably substantially 100%, for identifying infected infants, such that the number of infected infants with negative test results is minimal. A high negative predictive value and sensitivity allows identifying substantially all infected infants in a population of tested infants.

The health consequences of misdiagnosing uninfected neonates are substantially less severe than those of misdiagnosing infected neonates. It is desirable, however, that the test have a low false positive rate so that the number of misdiagnosed uninfected neonates is minimized. It is thus desirable that the test have a high positive predictive value (probability that a positive result is correct) and specificity (number of uninfected patients identified by the test as a fraction of actual number of uninfected patients). In particular, the positive predictive value and specificity of a test of the present invention are higher than 80%, preferably higher than 90%. An infection indicator of the present invention preferably allows a high positive predictive value and specificity.

Since neonatal sepsis is often fatal within hours of patient exposure to antigen, decisions to treat neonates perceived to be at risk for infection must be made rapidly, typically at initial evaluation of the neonates. A predictive (rather than confirmatory) test for excluding infection in neonates thus requires that test results be available rapidly, before decisions to treat infants with antibiotics or to confine the infants to a neonatal intensive care unit for observation and/or treatment. A rapid test of the present invention allows delaying treatment decisions until test results are available, with minimal risk to the infants. The level of an infection indicator of the present invention is a reliable indicator of infection within hours of neonatal exposure to antigen. The level of the infection indicator allows deciding whether to treat the neonate for infection at an initial evaluation of the neonate. The upregulation of the infection indicator in response to antigen occurs rapidly, and is preferably independent of antigen-induced protein synthesis.

The infection indicator is preferably a viral, bacterial and fungal infection indicator. Its level indicates whether the neonate has viral, bacterial, and/or fungal infection. The infection indicator is preferably a molecule.

To reduce the variability of test results, the level of the infection indicator preferably corresponds to a specific part of a whole blood sample, rather than to an average level of the infection indicator in the whole blood sample. Specific parts include serum, the surface of particular cell types, and the cytoplasm of particular cell types. Cell types include leukocytes, monocytes, and neutrophils, amond others. In a preferred embodiment, the measured level of the infection indicator is a level of the infection indicator on the surface of neutrophils.

In a preferred embodiment, the neutrophil surface level of CD11b (Mac-1, CR3) is used as a rapid infection indicator. It was found that neutrophil surface CD11b is a rapid and reliable indicator of infection in neonates. CD11b is a beta-integrin adhesion molecule involved in neutrophil adhesion, diapedesis and phagocytosis. For general information on CD11b, including its structure, see reference [21]. The protein is stored in primary and secondary intracellular granules within unstimulated neutrophils and certain other leukocytes, as described for example in references [22, 24, 34]. It is the receptor for C3bi, a component of the complement cascade. For information on the relationship between CD11b and complement see references [32–33].

CD11b is expressed on a variety of cells, including monocytes and neutrophils. It is normally expressed at very low levels on neutrophils and becomes elevated rapidly upon neutrophil encounter with pathogens or their products. CD11b increases on the neutrophil surface within 5 minutes of exposure to bacterial products such as endotoxin (lipopolysaccharide, LPS) in vitro, and surface expression peaks within 30 minutes, as illustrated in references [23–24]. Neutrophil upregulation of CD11b upon stimulation with LPS has been shown to depend on a complex but rapid cascade of events, initiated by the binding of LPS to CD14 on the neutrophil surface. In response to antigen, CD11b is transported from intracellular granules to the neutrophil surface. The upregulation of neutrophil surface CD11b expression is not dependent on antigen-induced protein synthesis. For further information on the mechanism of neutrophil CD11b upregulation in response to LPS see references [41–50].

Neutrophils are also known to increase expression of CD11b in vitro and in vivo upon stimulation with other factors such as the anaphylotoxin C5a, the bacterial product F-met-leu-phe, and the inflammatory cytokine tumor necrosis factor-alpha (TNF-α), probably through a mechanism unrelated to CD14. For information on neutrophil CD11b upregulation upon stimulation with such factors see references [46, 51–53]. Increase of neutrophil surface CD11b during viral and yeast infections has been reported in several in vivo and in vitro studies, including references [54–56].

CD11b is increased on adult neutrophils in vivo in settings of infection. The rapid upregulation of CD11b on neutrophils following exposure to pathogen has led to the suggestion that neutrophil surface CD11b may be useful as an early index of infection in adults (see references [23–24, 32–33, 35–40]). A study by Wakefield et al. [25] describes the use of CD11b as an early post-surgical indicator of sepsis in immunologically normal adults. The use of CD11b in immunodeficient patients such as neonates and immunocompromised patients has not been investigated, however, presumably in part because neutrophils from neonates generally contain less intracellular CD11b than do neutrophils from adults. Bruce et al. [26] and McEvoy et al. [27] have suggested that because neutrophil CD11b is decreased in neonatal neutrophils, the marker would not be likely to be useful as an indicator of neonatal infection.

Surprisingly, however, neutrophil surface CD11b upregulation in infected neonates is readily detectable within minutes of exposure to antigen. Surface CD11b becomes highly elevated within five minutes of exposure to antigen, and maximally elevated within thirty minutes. Despite its relatively low neonatal levels, neutrophil surface CD11b is a rapid, sensitive and specific indicator of neonatal infection.

A test of the present invention preferably uses a whole blood sample of the neonate. Neonatal blood draw allowances are based on the neonates weight, and are typically no more than a few milliliters. A neonates blood draw allowance is used for a variety of tests, each requiring a minimum amount of whole blood. It is thus preferred that a test of the present invention require as little whole blood as possible. The volume of whole blood required for the infection test is preferably on the order of 0.1 ml, ideally less than 0.2 ml. Analysis steps requiring large amounts of blood are therefore not desirable in a neonatal infection test of the present invention. Analysis steps requiring large amounts of blood include typical cell lysis and bulk cell separation (e.g. centrifugation) steps.

The whole blood sample is handled at all times under conditions inhibiting the spontaneous upregulation of neutrophil surface CD11b. In one embodiment, the sample is handled at 4° C. In another embodiment, a suitable quantity of a stabilizing compound such as adenosine or anti-CD14 antibody is added to the sample. Particular care should be taken in handling samples under analysis, since neutrophil surface CD11b assays are extremely sensitive to sample handling conditions. The consequences of inadequate control over assay conditions are illustrated by the study by Davis et al. [69], which reports no correlation between leukocyte levels of many markers, including CD11b, and the presence of infection in adults. Analysis of the methods in the Davis et al. study reveals that spontaneous upregulation of CD11b was not prevented: samples were analyzed up to 24 hours after collection, and were not stabilized by temperature control or addition of stabilizing compounds. Careful temperature control or addition of reagents to prevent spontaneous upregulation of CD11b is required to obtain consistent measurements of neutrophil surface CD11b.

Preferably, neutrophils are identified by flow cytometry in whole blood samples, according to a neutrophil identification marker. In a preferred embodiment the neutrophil identification marker comprises a CD15 marker such as a fluorescent anti-CD15 antibody. Identifying neutrophils from a whole blood sample is generally known in the art, and will not be discussed here in detail. The surface CD11b level is determined for each identified neutrophil according to a CD11b marker such as a fluorescent anti-CD11b antibody. The CD11b marker is spectrally distinguishable from the neutrophil identification marker, such that the two markers can be analyzed simultaneously on a two-laser flow cytometer. Fluorescent anti-CD15 and anti-CD11b antibodies are known in the art. The flow cytometry test described above is fast, easy to perform, and requires a very small amount of whole blood.

A level of a calibration marker is measured for determining an infection diagnosis threshold for the infection indicator. A relation between the diagnosis threshold and the level of the infection indicator in the neonate is used to determine whether to treat the patient for infection. The infection diagnosis threshold is chosen according to desired test sensitivity and specificity values. The diagnosis threshold is preferably chosen so as to avoid misdiagnosing infected patients.

In one embodiment, the diagnosis threshold corresponds to a sharp cutoff between infected and uninfected patient. The cutoff is then chosen such that it separates infected and uninfected patients with a negative predictive value of at least 99%. In another embodiment, multiple (e.g. two) diagnosis thresholds are used for identifying infected and uninfected subpopulations, as well as a subpopulation requiring further evaluation. A first diagnosis threshold separates uninfected patients and patients requiring evaluation, while a second threshold separates patients requiring evaluation and infected patients.

For a cell surface infection indicator, the calibration marker preferably comprises a microparticle coated with the infection indicator. The level of the infection indicator on the microparticle preferably corresponds to a sepsis diagnosis threshold. A separate calibration marker is needed for each diagnosis threshold.

In a preferred embodiment, the calibration marker comprises a CD11b-coated latex microparticle on the order of 1 $\mu$m in diameter. Techniques for generating microparticles coated with a particular molecule are well known in the art. In one such technique, microparticles are coated with mouse anti-latex antibodies conjugated to mouse anti-human CD11b antibodies. The coated microparticles are then exposed to CD11b. The level of CD11b on the microparticle is chosen to be substantially equal to the surface CD11b level on a neutrophil corresponding to the relevant diagnosis threshold. For calibration, the CD11b-coated microparticle is stained with the quantity of anti-CD11b fluorescent antibody used for staining neonatal neutrophils in the assay. The stained microparticle is analyzed on the device used for analyzing neonate samples, for calibrating the device's readings. For example, for a conventional flow cytometer, photomultiplier settings are preferably adjusted so that the fluorescence of anti-CD11b antibodies on the calibration microparticle corresponds to a predetermined level.

The calibration marker is preferably provided as part of a kit for testing neonates for infection. The kit comprises the calibration marker determining a diagnosis threshold for the neonates, a marker for the infection indicator, a neutrophil identification marker, and a stabilizing compound. In a preferred embodiment, the kit comprises CD11b-coated microparticles, fluorescent anti-CD11b antibodies, fluorescent neutrophil-specific antibodies spectrally distinguishable from the anti-Cd11b antibodies, and anti-CD14 antibodies. The concentrations of the kit components are chosen so as to yield a suitable (mid-range) infection indicator signal on the device used for analysis, for a given assay protocol.

The present invention further provides a method of diagnosing infection in immunodeficient patients. Immunodeficient patients include patients with immature immune systems (e.g. neonates), as well as immunocompromised patients. Immunocompromised patients include patients with HIV, and transplant patients on immunosuppressive medication. An infection diagnostic test is particularly useful in immunodeficient patients, for whom symptomatic diagnosis is much more difficult than in patients with normal immune systems. Different classes of immunodeficient patients generally have different suitable diagnosis thresholds. Consequently, diagnosis thresholds and kits for a class of immunodeficient patient are preferably tailored to the properties of the infection assay for that class.

The following examples are intended to illustrate particular aspects of the invention, and should not be construed to limit the invention.

EXAMPLE 1

Figure 1:
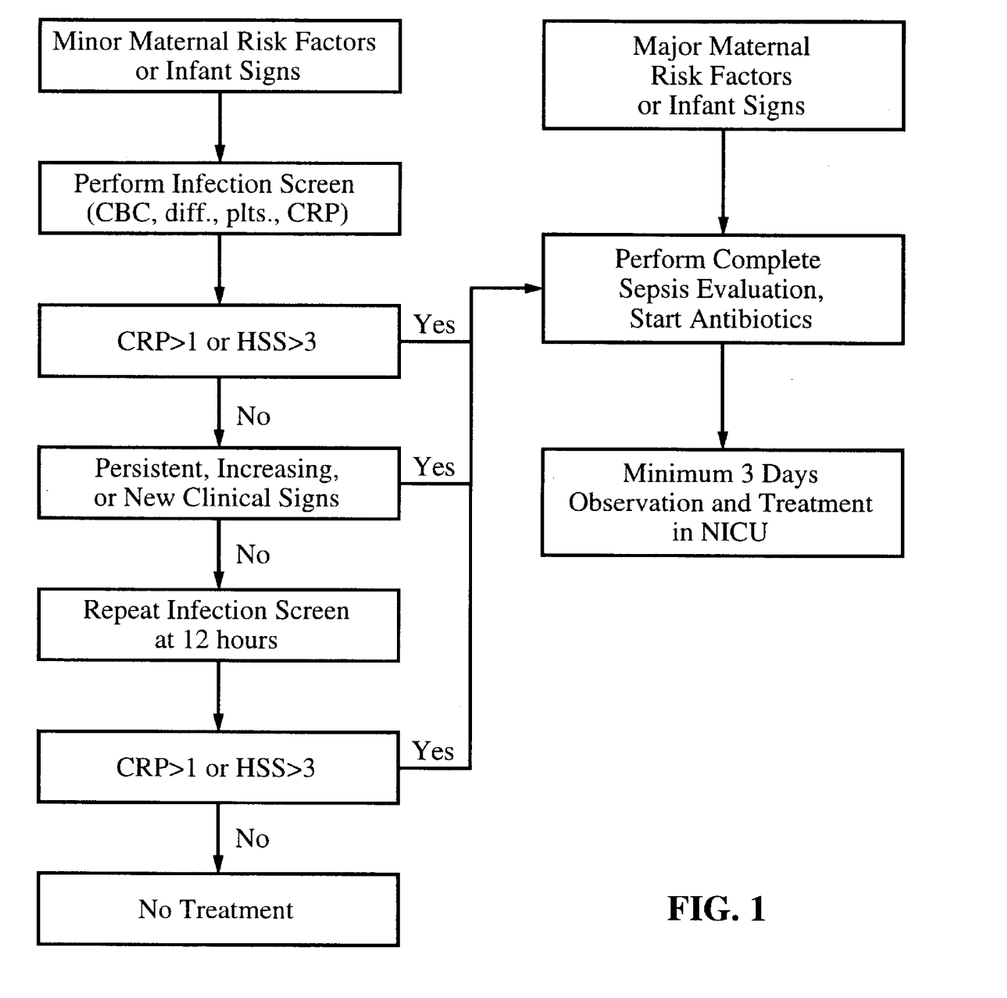
FIG. 1 is a flowchart summarizing inclusion and exclusion criteria and highlighting the critical path which guides the "Rule Out Infection" workup at Lucile Salter Packard Children's Hospital at Stanford.

A method of the present invention was used to evaluate neonates over 28 weeks of gestation who were admitted, on the first day of life, to the Neonatal Intensive Care Unit at Lucile Salter Packard Children's Hospital between August 1994 and January 1995. FIG. 1 summarizes inclusion and exclusion criteria and highlights the critical path which guides the "Rule Out Infection" workup at Lucile Salter Packard Children's Hospital at Stanford. A positive measurement on a CRP or hematological scoring system (HSS) test leads to a start of treatment. Such measurements cannot be used as infection indicators at early time points, however, as they do not permit excluding infection in evaluated neonates. At later time points and in the absence of persistent clinical signs, CRP becomes reliable enough to be used as a confirmatory infection indicator.

Subjects were enrolled if the reason for admission to the NICU was perceived risk for infection, either because of maternal intrapartum risk factors or infant symptoms. Admission to the NICU and determination of risk for infection was made by the attending pediatrician, not affiliated with this study, in accordance with the NICU critical pathway shown in FIG. 1. To avoid miscategorization of symptomatic infants in the Suspected Infection group, those with confirmed diagnoses that accounted for symptoms were not included in the Suspected Infection group. This study was approved by the Stanford University Human Subjects Committee. Because samples were obtained only as waste from clinically indicated blood draws, the requirement for informed consent was waived, and this study did not affect infant treatment or outcome.

Samples for CD11b measurement were obtained on the day of admission, concurrently with blood drawn for routine bacterial culture, blood counts and CRP measurement by the hospital's diagnostic facility. Gestational age and weight were also recorded at this time. Viral cultures were performed only as clinically indicated. Results of serum CRP and blood, urine and CSF cultures were collected at least 7 days later. Clinical signs of infection were recorded in the infant's chart by NICU nursing staff unaffiliated with the study. Risk factors, maternal pre-treatment with antibiotics, discharge diagnoses, clinical signs of infection (as noted in the infant's chart) were recorded by a party blinded to CRP and CD11b results.

EXAMPLE 2

Figure 2:
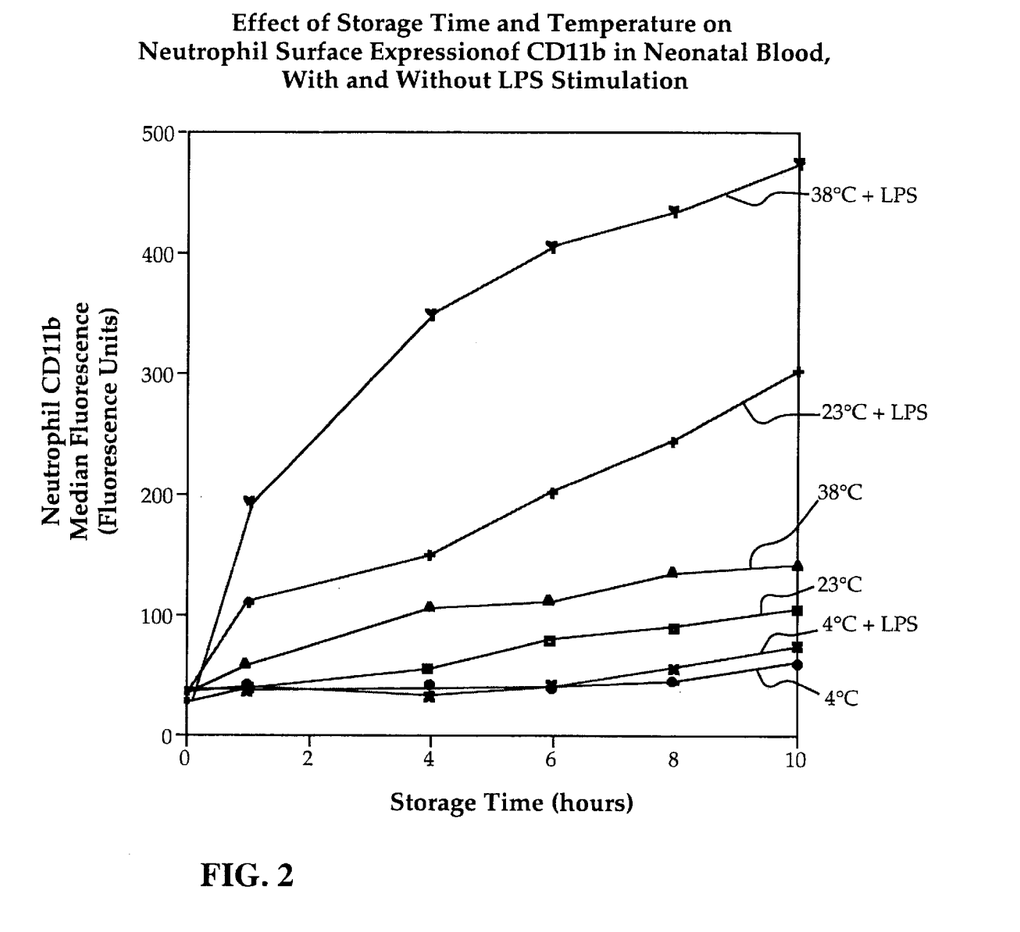
FIG. 2 illustrates the effects of time and temperature on neutrophil surface expression of CD11b, with and without LPS stimulation, according to the present invention.

The dependence of neutrophil surface CD11b level on sample storage time, temperature, and LPS presence was investigated in vitro and is shown in FIG. 2. Neutrophil CD11b does not increase appreciably on the neutrophil surface when samples are maintained at 4° C. for up to eight hours. A slight increase is noted in LPS stimulated and unstimulated cells after eight hours. Neutrophil surface CD11b does increase on cells stored at room temperature for greater than 2 hours, and on cells stored at 38° C. almost immediately. Cells stimulated with LPS at room temperature and at 38° C. showed the largest magnitude increase in neutrophil surface expression of CD11b.

EXAMPLE 3

CD11b expression on peripheral blood neutrophils was determined by flow cytometry of whole blood samples. Blood (0.1 ml) was obtained from at-risk infants admitted to the NICU, stained with antibodies detecting CD11b and CD15, chilled and analyzed within 8 hours of collection. Blood for culture, blood counts and C-Reactive Protein (CRP) determination was obtained simultaneously. Samples used for CD11b analyses were handled at 4° C., because CD11b upregulates spontaneously on neutrophils in peripheral blood samples at room temperature (see FIG. 2 and references [28–30]).

During blood draw for clinically indicated diagnostic studies, 0.1 ml of whole blood was obtained from each subject and was diluted with 2.5 ml cold staining medium. Staining medium was composed of deficient RPMI 1640 Medium (Applied Scientific, Irvine, Calif.), 1% fetal calf serum (Gemini Bioproducts, Calabasas, Calif.) with 1 M HEPES, pH 7.2 (Sigma, St. Louis, Mo.). 10% Sodium Azide stock solution was added to a concentration of 0.02%. If stored, samples were maintained at 4° C. for up to 8 hours. Samples were washed once with staining medium, resuspended in 0.5 ml staining medium and stained for 15 minutes with FITC-conjugated CD15 (to identify neutrophils) and PE-conjugated CD11b mouse anti-human monoclonal antibodies (Becton-Dickinson, Milpitas, Calif.). Samples were then washed three times and resuspended in 1% para-formaldehyde/staining medium. Prior to staining, the FITC-conjugated anti-CD15 was diluted with unconjugated anti-CD15 antibody in order to bring the neutrophil CD15 staining into mid-range on the Fluorescence Activated Cell Sorter (FACS) (FACScan, Becton Dickinson). The instrument was adjusted so that the fluorescence of standard beads (3.2 $\mu$m Sphero Rainbow Fluorescent Particles, Sphertech, Inc., Libertyville, Ill.) in each fluorescence channel was exactly the same for each run.

Samples were analyzed on the FACScan with a threshold set such that only cells with the correct range of CD15 fluorescence for neutrophils were accepted as events. This threshold excludes erythrocytes and all other leukocytes. The median fluorescence of neutrophil CD11b was determined for each sample based on the distribution of CD11b fluorescence per 30,000 cells counted and ranged from 1 to 475 fluorescence units (arbitrary units).

Cultured U-937 cells (ATCC, Rockville, Md.), which express low levels of CD11b and CD15, were stained and analyzed concurrently with patient samples to verify the staining procedure. Over the period of this study, U-937 cells were analyzed 100 times, with a mean ±SD of 2.00±0.11 for CD11b fluorescence. For information on CD11b expression in U-937 cells see reference [31].

EXAMPLE 4

Serum CRP levels were measured for all neonates using the standard assay protocol at Lucile Packard Children's Hospital at Stanford. Measured serum CRP levels ranged from <0.4–8.0. The CRP assay performed by the hospital's diagnostic facility has a lower limit of sensitivity of 0.4 mg/dl. CRP levels below this threshold are reported categorically (as "<0.4 mg/dl") rather than quantitatively. Levels greater than 1 were defined as abnormal in accordance with clinical protocol at Lucile Packard Children's Hospital at Stanford.

EXAMPLE 5

Figure 3:
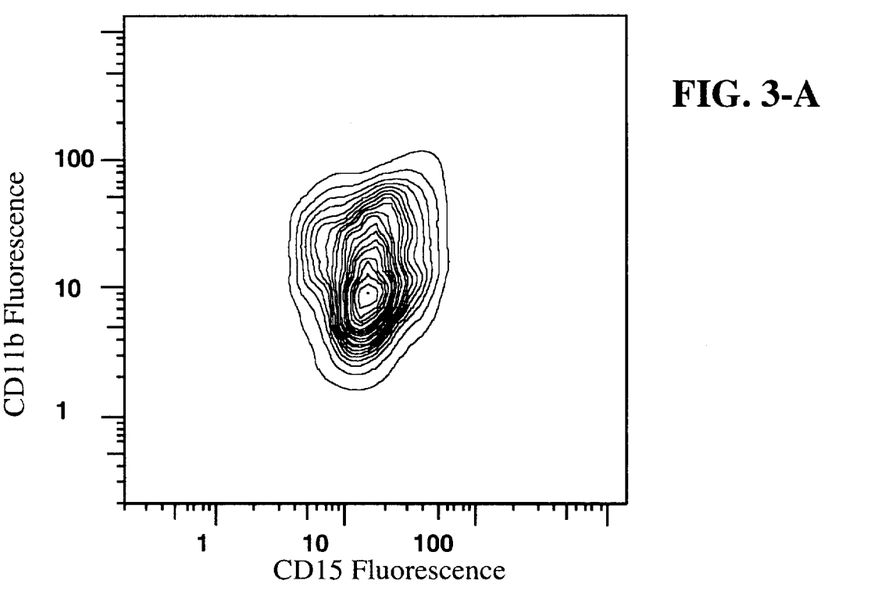

FIGS. 3-A and 3-B show sample FACS plots for an uninfected and a Group B Streptococcus-infected infant, respectively. Each contour represents 5% of the sample of 30,000 cells. Note that the fluorescence scale is logarithmic. The uninfected infant had low CD11b expression (median fluorescence=1.62), while the infected infant showed elevated CD11b (median fluorescence=245.00). The sample CD11b fluorescence is distributed tightly, indicating little interference from nonspecific binding. Although a hard gate was set on the FACScan so that only neutrophils were counted as events, further analysis gates were not necessary, as each sample clearly represents only one population of cells.

EXAMPLE 6

After results of all confirmatory tests became available, subjects were classified into Infection (positive bacterial or viral cultures, elevated CRP or WBC count, or strong and persistent clinical signs of infection) and No Infection (negative cultures, normal CRP over 3 days, no clinical signs of infection) groups. The Infection group was in turn subdivided into Confirmed Infection (positive bacterial or viral cultures) and Suspected Infection (negative cultures but elevated CRP or WBC count, or strong and persistent clinical signs of infection) groups. Assignment to all outcome groups was carried out by a party blinded to CD11b results. Clinical signs of infection leading to placement in the Suspected Infection group included one or more of the following conditions noted in the chart over greater than 8 hours, or two or more noted for greater than 4 hours: fever, hypothermia, exanthem or respiratory distress. Infants were included in this group only when a non-infectious etiology could not be identified to account for clinical signs. Such non-infectious etiologies include, but are not limited to, congenital malformations, drug withdrawal, and chromosomal anomalies including Trisomies 18 and 21.

Table 1 summarizes data obtained for 106 subjects. Statistical analysis was performed using JMP software (SAS Institute, Cary, N.C.), version 3.1. Differences in outcome groups were assessed using the G-test of independence for 2×3 and 2×2 contingency tables, as appropriate for this data. Of 106 subjects, 7 had positive bacterial or viral cultures ("Culture-confirmed infection"), 17 had clinical signs of infection but negative cultures ("Suspected infection"), and 82 had negative cultures and no clinical signs ("No infection"). Neutrophil CD11b was high in every infant with a positive bacterial culture of 106 subjects tested for bacteria (3 cases of Group B Streptococcus, 1 case of Group D Streptococcus, 1 case of Enterococcus Faecalis) and was also elevated in two subjects with positive viral cultures of 11 subjects tested for virus (Herpes Simplex Virus and Coxsackie B Virus). Both infants with positive viral cultures had elevated CD11b, but the CRP levels remained within normal limits.

TABLE 1

| Outcome Group | Number in Group | Number Cultured | Neutrophil CD11b > 60 | Peak Serum CRP > 1 |
|---|---|---|---|---|
| Culture-Confirmed Infection (Total) | 7 | | 7 | 5 |
| Culture-Confirmed Bacterial Infection | 5 | 106 | 5 | 5 |
| Culture-Confirmed Viral Infection | 2 | 11 | 2 | 0 |
| Suspected Infection | 17 | | 16 | 15 |
| No Infection | 82 | | 0 | 2 |
| Total | 106 | | 23 | 22 |

Table 2 shows the CD11b and CRP levels for the seven infants with positive cultures. CRP was elevated by day 3 in those infants with positive bacterial cultures, but was not elevated in those infants with positive viral cultures. In 82 of 106 infants (77%), infection was excluded by negative cultures and by the absence of clinical signs of infection. None of these infants had high CD11b.

TABLE 2

| Cultured Organism | Median Neutrophil CD11b | Serum CRP |
|---|---|---|
| Group B Strep | 426 | 4 |
| Group B Strep | 468 | 3.5 |
| Group B Strep | 146 | 2.4 |
| Group D Strep | 100 | 1 |
| Enterococcus Faecalis | 110 | 1.6 |
| Coxsackie B Virus | 184 | <0.4 |
| Herpes Simplex Virus | 174 | 0.5 |

Figure 4:
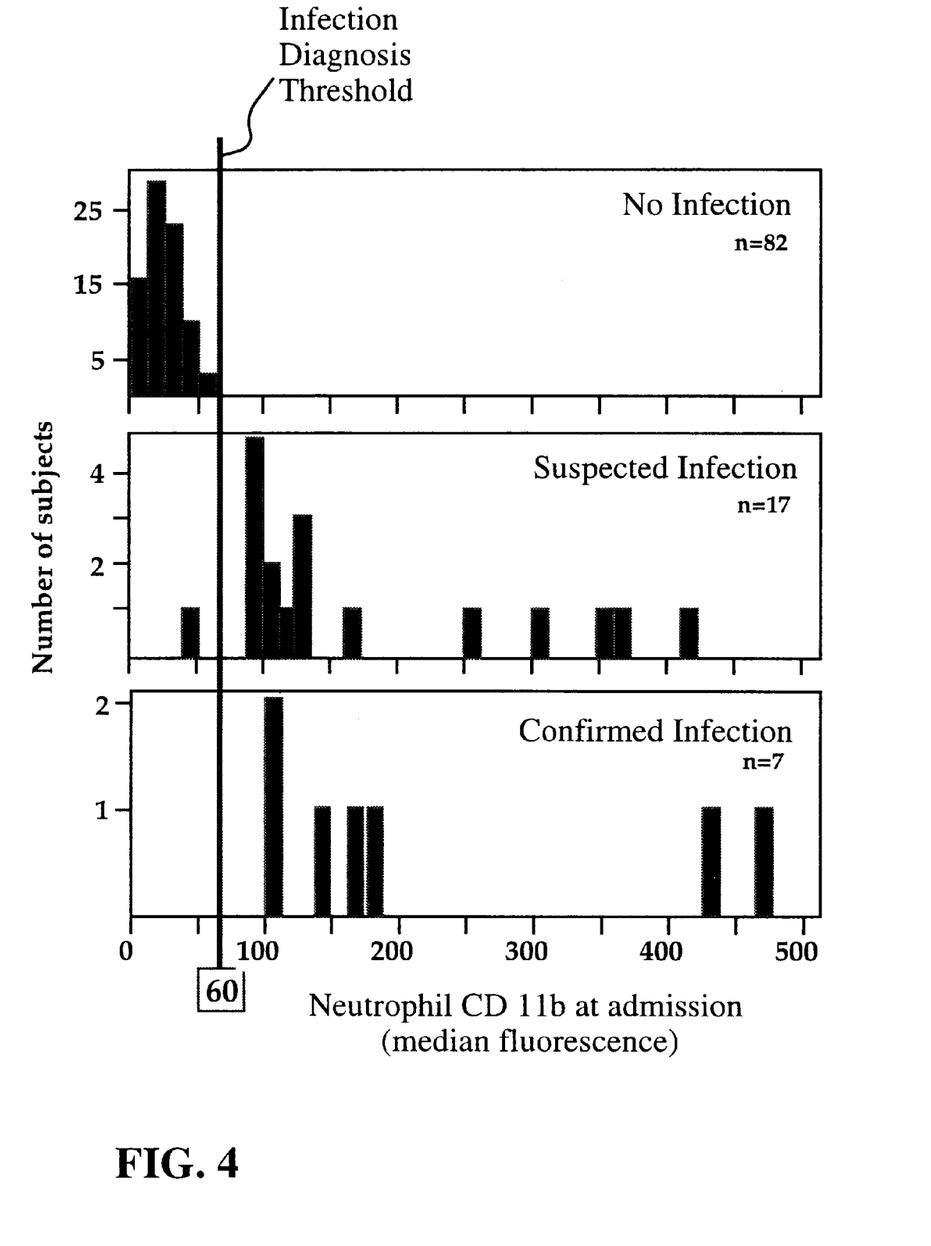

FIGS. 4-A through 4-C show the distribution of neutrophil CD11b levels for each outcome group. Neutrophil CD11b was elevated in all infants with culture-confirmed infection, 94% with suspected infection, and none with no infection. A diagnosis threshold was defined at 60 fluorescence units, based on the distribution of fluorescence values for each outcome group. CD11b was greater than 100 median fluorescence in all subjects in the "Confirmed infection" group and less than 60 median fluorescence in the "No infection" group. In the "Suspected infection" group, neutrophil CD11b was greater than 60 median fluorescence in all but one subject. Infection was suspected in this subject due to persistent hypothermia. CRP levels were low in this infant as well.

Table 3 shows the sensitivity, specificity, positive and negative predictive values of the CD11b assay in detecting infection for the following groups of infants: 1) Infected Neonates (Suspected or Confirmed Infection) (n=17, 96% sensitive and 100% specific); 2) Bacterial or Viral Infection Confirmed (n=7, a subset of group 1, 100% sensitive and 83% specific); 3) Bacterial Infection Confirmed (n=5, a subset of groups 1 and 2, 100% sensitive and 81% specific). Based on the G statistic, these values were all significant at $p < 10^{-4}$. The Infected Neonates grouping is most important, as a safe test should identify all neonates likely to be infected. The negative and positive predictive values, sensitivity and specificity were 100%, 99%, 96% and 100%, respectively, for diagnosis of neonatal infection at initial evaluation. The negative predictive value of neutrophil CD11b for identifying suspected or confirmed infection was 99%, with a 95% confidence interval of 96.4–100%.

TABLE 3

| Outcome Group | n | G test | p | Sensitivity | Specificity | NPV | PPV |
|---|---|---|---|---|---|---|---|
| Infection Suspected or Confirmed | 17 | 98.99 | $3 \times 10^{-23}$ | 96% | 100% | 99% | 100% |
| Bacterial or Viral Infection Confirmed | 7 | 20.87 | $5 \times 10^{-6}$ | 100% | 83% | 100% | 30% |
| Bacterial Infection Only Confirmed | 5 | 13.80 | $2 \times 10^{-4}$ | 100% | 81% | 100% | 22% |

Figure 5:
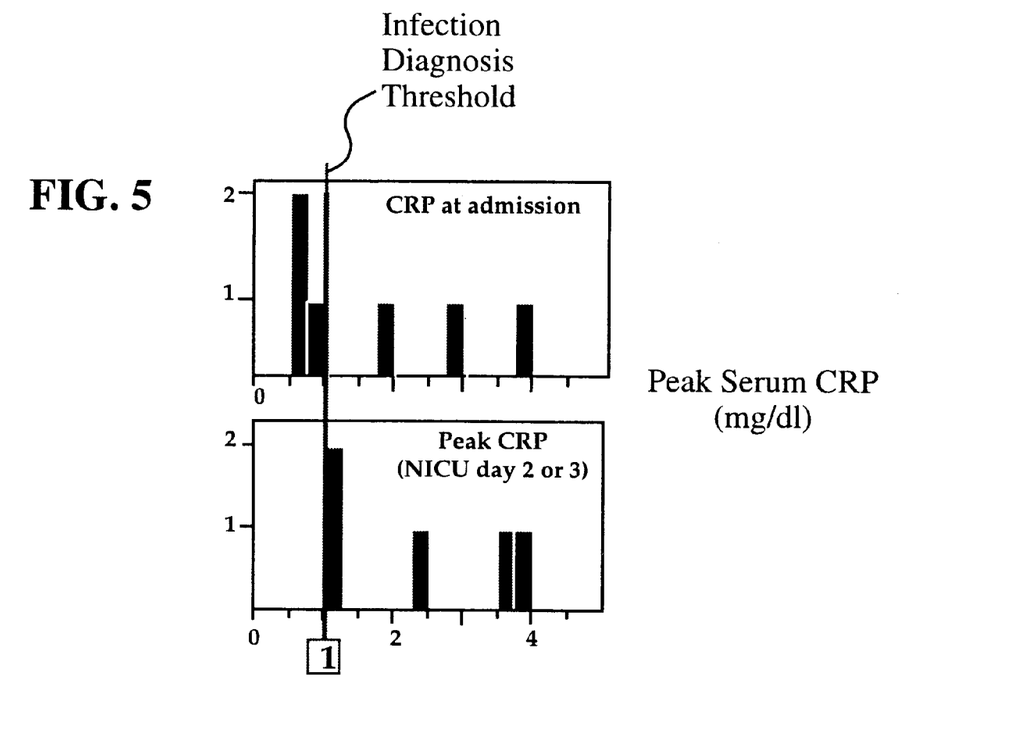

FIGS. 5-A and 5-B show the distribution of CRP on day of admission and peak CRP in neonates with positive bacterial cultures, respectively. All patients in the Confirmed Infection group had high neutrophil CD11b on hospital day 1. However, 3 of the 5 infants in this group did not develop an elevated serum CRP until at least hospital day 2. Blood cultures were sent on hospital day 1, and thus reflect infection present at the time of the first CRP measurement and at the time of the CD11b measurement. CD11b elevation preceded CRP elevation in 60% of neonates whose bacterial blood cultures were subsequently positive. In the Confirmed Infection group, two subjects had positive viral cultures. These subjects had low CRP but elevated CD11b.

Figure 6:
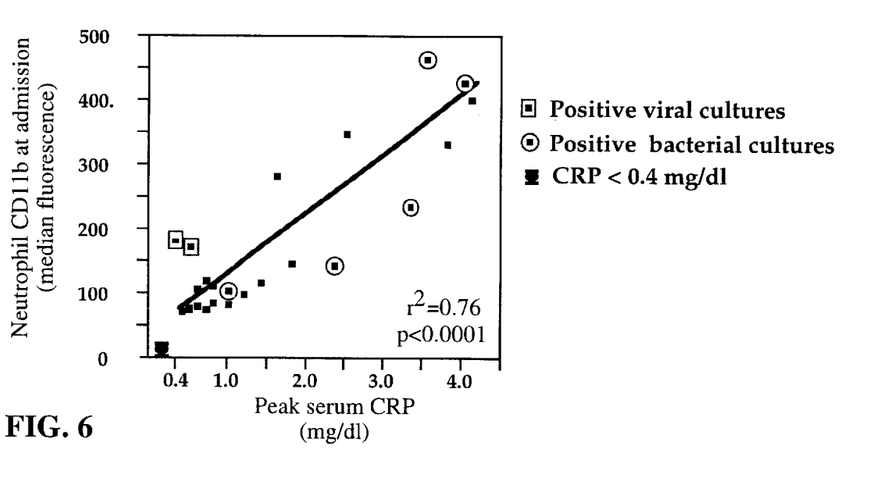
FIG. 6 illustrates the relationship between neutrophil CD11b and highest measured serum CRP in infants evaluated for infection, according to the present invention.

FIG. 6 demonstrates that elevated CD11b on neutrophils is correlated with peak CRP ($r^2=0.76$, $p<0.0001$) for CRP values larger than 0.4. Correlation was assessed using a standard linear regression. The CRP value included in this figure was the highest value obtained over a three day period, while the CD11b value was obtained on admission. Subjects with CRP less than 0.4 were omitted from this linear regression, as the CRP assay has a limit to sensitivity of 0.4. The data omitted from the linear regression is shown as the mean with error bars at CRP=0.3. Correlation between CD11b and peak CRP levels was assessed for combined categorical and continuous data using the Spearman Rho measure of association, which allows inclusion of the categorical data ("CRP<0.4"). For n=26 observations, the Spearman-Rho test yielded $r^2=0.54$, $p<0.0001$.

No significant relationship was found between elevation or reduction in white blood cell subpopulations measured by the CBC (e.g. segmented neutrophils, bands (immature neutrophils), lymphocytes) and positive blood cultures or clinical signs of infection on an individual basis or by outcome group. No relationship was found between white blood cell subpopulations and elevated CD11b or elevated CRP. In the two individuals with positive viral cultures, lymphocyte counts were not significantly different from those with positive bacterial cultures. No relationships were found between Apgar scores, birth weights or gestational ages and CD11b, CRP, positive bacterial cultures or clinical outcome groups.

It will be clear to one skilled in the art that the above embodiments may be altered in many ways without departing from the scope of the invention. For example, many markers other than fluorescent antibodies are suitable for use in a method of the present invention. Such markers include, among others, enzymes, polynucleotides, and sugars. Many analysis techniques other than fluorescence activated cell sorting are suitable in a method of the present invention, including scanning microscopy and light refraction techniques. In addition, assay techniques not involving analysis of specific blood parts or cell types are suitable for use in the present invention. Such techniques include whole blood staining only with a marker for the infection indicator, followed by flow cytometric or laser scanning microscopy analysis of the entire blood sample. Various clinical techniques are available for distinguishing infected and uninfected patients. Test parameters, including diagnosis thresholds, can be chosen according to particular clinical applications and required positive and negative predictive values. Accordingly, the scope of the invention should be determined by the following claims and their legal equivalents.

LIST OF CITED REFERENCES

1. Ohlsson A, Lacy J. Perinatal clinical epidemiology. *Curr Opin Pediatr* 1993; 5:142–9.
2. Witek-Janusek L, Cusack C. Neonatal infection: confronting the challenge. *Crit Care Nurs Clin North Am* 1994; 6:405–19.
3. Kotagal U R, Perlstein P H, Gamblian V, Donovan E F, Atherton H D. Description and evaluation of a program for the early discharge of infants from a neonatal intensive care unit [see comments]. *J Pediatr* 1995; 127:285–90.
4. Gerdes J S. Clinicopathologic approach to the diagnosis of neonatal infection. *Isr J Med Sci* 1994; 30:430–41.
5. Gerdes J S. Clinicopathologic Approach to the Diagnosis of Neonatal Infection. *Clinics in Perinatology* 1991; 18:361–81.
6. Germain M, Krohn M A, Daling J R. Reproductive history and the risk of neonatal infection. *Paediatr Perinat Epidemiol* 1995; 9:48–58.
7. Anderson D C. Neonatal neutrophil dysfunction [editorial; comment]. *J Lab Clin Med* 1992; 120:816–7.
8. Rosenfeld C R. Band neutrophil counts in neonates [letter; comment]. *J Pediatr* 1995; 126:504–6.
9. Rowen J L, Smith C W, Edwards M S. Group B streptococci elicit leukotriene B4 and interleukin-8 from human monocytes: neonates exhibit a diminished response. *J Infect Dis* 1995; 172:420–6.
10. Tan N D, Davidson D. Comparative differences and combined effects of interleukin-8, leukotriene B4, and platelet-activating factor on neutrophil chemotaxis of the newborn. *Pediatr Res* 1995; 38:11–6.
11. Crockett M. Physiology of the neonatal immune system. *J Obstet Gynecol Neonatal Nurs* 1995; 24:627–34.
12. Holt P G. Postnatal maturation of immune competence during infancy and childhood. *Pediatr Allergy Immunol* 1995; 6:59–70.
13. Wolach B, Carmi D, Gilboa S, et al. Some aspects of the humoral immunity and the phagocytic function in newborn infants. *Isr J Med Sci* 1994; 30:331–5.
14. Rouse D J, Goldenberg R L, Cliver S P, Cutter G R, Mennemeyer S T, Fargason C A, Jr. Strategies for the prevention of early-onset neonatal group B streptococcal infection: a decision analysis. *Obstet Gynecol* 1994; 83:483–94.
15. Escobar G J, Fischer A, Li D K, Kremers R, Armstrong M A. Score for neonatal acute physiology: validation in three Kaiser Permanente neonatal intensive care units. *Pediatrics* 1995; 96:918–22.
16. Yancey M K, Duff P, Kubilis P, Clark P, Frentzen B H. Risk factors for neonatal infection. *Obstet Gynecol* 1996; 87:188–94.
17. Drews K, Szczapa J, Zak J, Andrzejewska R, Zak L, Mackiewicz A. Blood serum concentration of C-reactive protein and interleukin-6 in diagnosis of neonatal infections. *Ann N Y Acad Sci* 1995; 762:398–9.
18. Kawamura M, Nishida H. The usefulness of serial C-reactive protein measurement in managing neonatal infection. *Acta Paediatr* 1995; 84:10–3.
19. Kessler A, Grunert C, Wood W G. The limitations and usefulness of C-reactive protein and elastase-alpha 1-proteinase inhibitor complexes as analytes in the diagnosis and follow-up of infection in newborns and adults. *Eur J Clin Chem Clin Biochem* 1994; 32:365–8.
20. Schouten-Van Meeteren N Y, Rietveld A, Moolenaar A J, Van Bel F. Influence of perinatal conditions on C-reactive protein production [see comments]. *J Pediatr* 1992; 120:621–4.
21. Corbi A L, Kishimoto T K, Miller L J, Springer T A. The human leukocyte adhesion glycoprotein Mac-I (complement receptor type 3, CD11b) alpha subunit. Cloning, primary structure, and relation to the integrins, von Willebrand factor and factor B. *J Biol Chem* 1988; 263:12403–11.
22. Miller L J, Bainton D F, Borregaard N, Springer T A. Stimulated mobilization of monocyte Mac-1 and p150,95 adhesion proteins from an intracellular vesicular compartment to the cell surface. *J Clin Invest* 1987; 80:535–44.
23. Lehr H A, Krombach F, Munzing S, et al. In vitro effects of oxidized low density lipoprotein on CD11b/CD18 and L-selectin presentation on neutrophils and monocytes with relevance for the in vivo situation. *Am J Pathol* 1995; 146:218–27.
24. Simms H H, D'Amico R. Lipopolysaccharide induces intracytoplasmic migration of the polymorphonuclear leukocyte CD11b/CD18 receptor. *Shock* 1995; 3:196–203.
25. Wakefield C H, Carey P D, Foulds S, Monson J R, Guillou P J. Polymorphonuclear leukocyte activation. An early marker of the postsurgical infection response. *Arch Surg* 1993; 128:390–5.
26. Bruce MC, Baley J E, Medvik K A, Berger M. Impaired surface membrane expression of C3bi but not C3b receptors on neonatal neutrophils. *Pediatr Res* 1987; 21:306–11.
27. McEvoy L T, Zakem-Cloud H, Tosi M F. Total cell content of CR3 (CD11b/CD18) and LFA-1 (CD11a/CD18) in neonatal neutrophils: relationship to gestational age. *Blood* 1996; 87:3929–33.
28. Repo H, Jansson S E, Leirisalo-Repo M. Flow cytometric determination of CD11b upregulation in vivo. *J Immunol Methods* 1993; 164:193–202.
29. Repo H, Jansson S E, Leirisalo-Repo M. Anticoagulant selection influences flow cytometric determination of CD11b upregulation in vivo and ex vivo. *J Immunol Methods* 1995; 185:65–79.
30. Connall T P, Zhang J, Vaziri N D, Kaupke C J, Wilson S E. Leukocyte CD11b and CD18 expression are increased in blood salvaged for autotransfusion. *Am Surg* 1994; 60:797–800.
31. Ikewaki N, Tamauchi H, Inoko H. Modulation of cell surface antigens and regulation of phagocytic activity mediated by CD11b in the monocyte-like cell line U937 in response to lipopolysaccharide. *Tissue Antigens* 1993; 42:125–32.
32. Pettit E J, Hallett M B. Neutrophil activation and priming during engagement of CD11b/CD18 integrins. *Biochem Soc Trans* 1994; 22:327S.
33. Witthaut R, Farhood A, Smith C W, Jaeschke H. Complement and tumor necrosis factor-alpha contribute to Mac-1 (CD11b/CD18) up-regulation and systemic neutrophil activation during endotoxemia in vivo. *J Leukoc Biol* 1994; 55:105–11
34. Rebuck N, Finn A. Polymorphonuclear granulocyte expression of CD11a/CD18, CD11b/CD18 and L-selectin in normal individuals. *FEMS Immunol Med Microbiol* 1994; 8:189–95.

35. Simms H H, D'Amico R. Polymicrobial infection disrupts normal neutrophil extracellular matrix protein interactions. *Circ Shock* 1992; 38:1–8.
36. Anderson D C, Miller L J, Schmalstieg F C, Rothlein R, Springer T A. Contributions of the Mac-1 glycoprotein family to adherence-dependent granulocyte functions: structure-function assessments employing subunit-specific monoclonal antibodies. *J Immunol* 1986; 137:15–27.
37. Lo S K, Van Seventer G A, Levin S M, Wright S D. Two leukocyte receptors (CD11a/CD18 and CD11b/CD18) mediate transient adhesion to endothelium by binding to different ligands. *J Immunol* 1989; 143:3325–9.
38. Finn A, Strobel S, Levin M, Klein N. Endotoxin-induced neutrophil adherence to endothelium: relationship to CD11b/CD18 and L-selectin expression and matrix disruption. *Ann N Y Acad Sci* 1994; 725:173–82.
39. Lynam E B, Simon S I, Rochon Y P, Sklar L A. Lipopolysaccharide enhances CD11b/CD18 function but inhibits neutrophil aggregation. *Blood* 1994; 83:3303–11.
40. Simms H H, D'Amico R. Hypoxemia regulates effect of lipopolysaccharide on polymorphonuclear leukocyte CD11b/CD18 expression. *J Appl Physiol* 1994; 76:1657–63.
41. Wright S D. CD14 and innate recognition of bacteria. *J Immunol* 1995; 155:6–8.
42. Wurfel M M, Kunitake S T, Lichenstein H, Kane J P, Wright S D. Lipopolysaccharide (LPS)-binding protein is carried on lipoproteins and acts as a cofactor in the neutralization of LPS. *J Exp Med* 1994; 180:1025–35.
43. Wurfel M M, Wright S D. Lipopolysaccharide (LPS) binding protein catalyzes binding of LPS to lipoproteins. *Prog Clin Biol Res* 1995; 392:287–95.
44. Weingarten R, Sklar L A, Mathison J C, et al. Interactions of lipopolysaccharide with neutrophils in blood via CD14. *J Leukoc Biol* 1993; 53:518–24.
45. Qing G, Rajaraman K, Bortolussi R. Diminished priming of neonatal polymorphonuclear leukocytes by lipopolysaccharide is associated with reduced CD14 expression. *Infect Immun* 1995; 63:248–52.
46. Lynn W A, Liu Y, Golenbock D T. Neither CD14 nor serum is absolutely necessary for activation of mononuclear phagocytes by bacterial lipopolysaccharide. *Infect Immun* 1993; 61:4452–61.
47. Haziot A, Rong G W, Bazil V, Silver J, Goyert S M. Recombinant soluble CD14 inhibits LPS-induced tumor necrosis factor-alpha production by cells in whole blood. *J Immunol* 1994; 152:5868–76.
48. Haziot A, Tsuberi B Z, Goyert S M. Neutrophil CD14: biochemical properties and role in the secretion of tumor necrosis factor-alpha in response to lipopolysaccharide. *J Immunol* 1993; 150:5556–65.
49. Froon A H, Dentener M A, Greve J W, Ramsay G, Buurman W A. Lipopolysaccharide toxicity-regulating proteins in bacteremia. *J Infect Dis* 1995; 171:1250–7.
50. Frey E A, Miller D S, Jahr T G, et al. Soluble CD14 participates in the response of cells to lipopolysaccharide. *J Exp Med* 1992; 176:1665–71.
51. Ross G D, Vetvicka V. CR3 (CD11b, CD18): a phagocyte and NK cell membrane receptor with multiple ligand specificities and functions. *Clin Exp Immunol* 1993; 92:181–4.
52. Scannell G, Waxman K, Vaziri N D, et al. Effects of trauma on leukocyte intercellular adhesion molecule-1, CD11b, and CD18 expressions. *J Trauma* 1995; 39:641–4.
53. Wollner A, Wollner S, Smith J B. Acting via A2 receptors, adenosine inhibits the upregulation of Mac-1 (Cd11b/CD18) expression on FMLP-stimulated neutrophils. *Am J Respir Cell Mol Biol* 1993; 9:179–85.
54. McFarland H I, Nahill S R, Maciaszek J W, Welsh R M. CD11b (Mac-1): a marker for CD8+ cytotoxic T cell activation and memory in virus infection. *J Immunol* 1992; 149:1326–33.
55. Roberts R L, Ank B J, Stiehm E R. Antiviral properties of neonatal and adult human neutrophils. *Pediatr Res* 1994; 36:792–8.
56. Newman S L, Chaturvedi S, Klein B S. The WI-1 antigen of Blastomyces dermatitidis yeasts mediates binding to human macrophage CD11b/CD18 (CR3) and CD14. *J Immunol* 1995; 154:753–61.
57. Radetsky M. The Laboratory Evaluation of Newborn Infection. *Current Opinion in Infectious Diseases* 1995; 8:191–99.
58. Spear M L, Stefano J L, Fawcett P, Proujansky R. Soluble interleukin-2 receptor as a predictor of neonatal infection. *J Pediatr* 1995; 126:982–5.
59. Da Silva O, Ohlsson A, Kenyon C. Accuracy of leukocyte indices and C-reactive protein for diagnosis of neonatal infection: a critical review. *Pediatr Infect Dis J* 1995; 14:362–6.
60. Rodwell R L, Taylor K M, Tudehope D I, Gray P H. Hematologic scoring system in early diagnosis of infection in neutropenic newborns. *Pediatr Infect Dis J* 1993; 12:372–6.
61. Williamson M, Fraser S H, Tilse M. Failure of the urinary group B streptococcal antigen test as a screen for neonatal infection. *Arch Dis Child Fetal Neonatal Ed* 1995; 73:F109–11.
62. Hachey W E, Wiswell T E. Limitations in the usefulness of urine latex particle agglutination tests and hematologic measurements in diagnosing neonatal infection during the first week of life. *J Perinatol* 1992; 12:240–5.
63. Salzer H R, Pollak A, Herkner K, Weninger M, Schemper W. Value of measurement of neutrophil elastase-alpha 1 proteinase inhibitor levels in the early diagnosis of neonatal infection. *Eur J Clin Microbiol Infect Dis* 1993; 12:553–6.
64. Buck C, Bundschu J, Gallati H, Bartmann P, Pohlandt F. Interleukin-6: a sensitive parameter for the early diagnosis of neonatal bacterial infection. *Pediatrics* 1994; 93:54–8.
65. Rodwell R L, Leslie A L, Tudehope D I. Early diagnosis of neonatal infection using a hematologic scoring system. *J Pediatr* 1988; 112:761–7.
66. Leibovich M, Gale R, Slater P E. Usefulness of the gastric aspirate examination in the diagnosis of neonatal infection. *Trop Geogr Med* 1987; 39:15–7.
67. Gendrel D, Assicot M, Raymond J, et al. Procalcitonin as a marker for the early diagnosis of neonatal infection. *J Pediatr* 1996; 128:570–3.
68. Lin R Y, Astiz M E, Saxon J C, Rackow E C. Altered leukocyte immunophenotypes in septic shock. Studies of HLA-DR, CD11b, CD14, and IL-2R expression. *Chest* 1993; 104:847–53.
69. Davis B H, Bigelow N C, Curnutte J T, Ornvold K. Neutrophil CD64 expression: Potential diagnostic indicator of acute inflammation and therapeutic monitor of interferon-gamma therapy. *Laboratory Hematology* 1995; 1:3–12.

What is claimed is:

1. A method of testing a neonate for infection, the method comprising:
   measuring neutrophil cell surface levels of CD11b in a sample from said neonate; and
   comparing said cell surface levels of CD11b to an infection diagnosis threshold;

wherein cell surface levels of CD11b that exceed said infection diagnosis threshold is indicative of infection.

2. The method of claim 1, wherein said method of testing is performed within four hours of an initial evaluation of said neonate.

3. The method of claim 1 wherein said measuring is performed by flow cytometry.

4. The method of claim 1 wherein said sample is a whole blood sample of less than 0.2 ml volume.

5. The method of claim 1 wherein said measuring step comprises direct binding of a labeled marker to neutrophil CD11b.

6. The method of claim 1, wherein said sample is exposed to a condition inhibiting spontaneous upregulation of CD11b.

7. The method of claim 6 wherein said condition comprises a temperature substantially equivalent to 4° C.

8. The method of claim 6, wherein said condition comprises a stabilizing compound.

9. The method of claim 1 wherein said infection comprises a bloodstream infection.

10. The method of claim 1, wherein neutrophils are identified by detecting the specific binding of a neutrophil identification marker.

11. A method of testing a population of neonates for infection, the method comprising:

measuring neutrophil cell surface levels of CD11b in samples from said population of neonates;

determining the presence of infection in said neonates;

correlating the cell surface level of CD11b to the presence of infection;

wherein an infection diagnosis threshold is determined to be the cell surface level of CD11b that is present in infected samples.

12. The method of claim 11 wherein samples having a neutrophil cell surface level of CD11b above said infection diagnosis threshold comprises substantially all infected neonates in said population.

13. The method of claim 12 wherein a sensitivity of said method is substantially 100%.

14. The method of claim 13, wherein a specificity of said method is higher than 90%.

15. The method of claim 11 wherein said samples having a neutrophil cell surface level of CD11b below said infection diagnosis threshold consist substantially of uninfected neonates.

16. The method of claim 1, wherein said step of measuring neutrophil cell surface level of CD11b comprises:

binding of a labeled CD11b-specific antibody to said neutrophil; and detecting the level of label bound to said neutrophil.

17. The method of claim 16 wherein said labeled CD-11b-specific antibody is a fluorescent antibody.

18. The method of claim 1 wherein said step of measuring neutrophil expression of CD11b comprises:

measuring intensity of an optical signal from a marker bound to CD11b.

19. A kit for testing a neonate for infection, the kit comprising:

a calibration marker for determining the infection diagnosis threshold of neutrophil expression of CD11b, wherein said calibration marker comprises the amount of CD11b that is representative of the amount of CD11b on a neutrophil from an infected sample.

20. The kit of claim 19, wherein said calibration marker comprises a CD11b-coated microparticle.

21. The kit of claim 19, further comprising a marker that specifically detects CD11b.

22. The kit of claim 21 wherein said marker that specifically detects CD11b is a fluorescent anti-CD11b antibody.

23. The kit of claim 21 further comprising a cell type identification marker for identifying neutrophils.

24. The kit of claim 23, wherein said marker for identifying neutrophils comprises a fluorescent antibody.

25. The kit of claim 19, further comprising a stabilizing compound for inhibiting a spontaneous upregulation of CD11b in said sample.

26. The kit of claim 25, wherein said stabilizing compound is selected from the group consisting of adenosine and anti-CD14 antibody.

27. The kit of claim 19, further comprising:

a) a marker that specifically detects CD11b;

b) a neutrophil identification marker; and c) a stabilizing compound for inhibiting a spontaneous upregulation of CD11b in a sample.

28. The kit of claim 27, wherein:

a) said marker that specifically detects CD11b comprises a first fluorescent antibody;

b) said neutrophil identification marker comprises a second fluorescent antibody spectrally distinguishable from said first fluorescent antibody; and c) said stabilizing compound is selected from the group consisting of adenosine and anti-CD14 antibody.

* * * * *